United States Patent
Roe et al.

(10) Patent No.: US 8,170,241 B2
(45) Date of Patent: May 1, 2012

(54) MOBILE TELE-PRESENCE SYSTEM WITH A MICROPHONE SYSTEM

(75) Inventors: David Bjorn Roe, Santa Barbara, CA (US); Daniel Steven Sanchez, Summerland, CA (US); Marco Pinter, Santa Barbara, CA (US); Derek Walters, Goleta, CA (US); Charles S. Jordan, Santa Barbara, CA (US)

(73) Assignee: Intouch Technologies, Inc., Goleta, CA (US)

( * ) Notice: Subject to any disclaimer, the term of this patent is extended or adjusted under 35 U.S.C. 154(b) by 1045 days.

(21) Appl. No.: 12/148,464

(22) Filed: Apr. 17, 2008

(65) Prior Publication Data

US 2010/0019715 A1    Jan. 28, 2010

(51) Int. Cl.
    *H04R 3/00*    (2006.01)

(52) U.S. Cl. ............ 381/122; 381/26; 381/91; 381/355; 381/356

(58) Field of Classification Search ............... 381/26, 381/91, 122, 355, 365
    See application file for complete search history.

(56) References Cited

U.S. PATENT DOCUMENTS

| | | |
|---|---|---|
| 4,413,693 A | 11/1983 | Derby |
| 4,638,445 A | 1/1987 | Mattaboni |
| 4,709,265 A | 11/1987 | Silverman et al. |
| 4,803,625 A | 2/1989 | Fu et al. |
| 4,875,172 A | 10/1989 | Kanayama |
| 4,977,971 A | 12/1990 | Crane, III et al. |
| 5,073,749 A | 12/1991 | Kanayama |
| 5,084,828 A | 1/1992 | Kaufman et al. |
| 5,130,794 A | 7/1992 | Ritchey |
| 5,341,242 A | 8/1994 | Gilboa et al. |
| 5,374,879 A | 12/1994 | Pin et al. |
| 5,441,047 A | 8/1995 | David et al. |
| 5,442,728 A | 8/1995 | Kaufman et al. |
| 5,462,051 A | 10/1995 | Oka et al. |
| 5,544,649 A | 8/1996 | David et al. |
| 5,553,609 A | 9/1996 | Chen et al. |
| 5,572,229 A | 11/1996 | Fisher |

(Continued)

FOREIGN PATENT DOCUMENTS

CA   2289697 A1   11/1998

(Continued)

OTHER PUBLICATIONS

F. Ando et al., "A Multimedia Self-service Terminal with Conferencing Functions", 1995, IEEE, pp. 357-362.

(Continued)

*Primary Examiner* — Victor A Mandala
(74) *Attorney, Agent, or Firm* — Paul Evans

(57) ABSTRACT

A remote controlled robot system that includes a robot and a remote control station. The robot includes a binaural microphone system that is coupled to a speaker system of the remote control station. The binaural microphone system may include a pair of microphones located at opposite sides of a robot head. The location of the microphones roughly coincides with the location of ears on a human body. Such microphone location creates a mobile robot that more effectively simulates the tele-presence of an operator of the system. The robot may include two different microphone systems and the ability to switch between systems. For example, the robot may also include a zoom camera system and a directional microphone. The directional microphone may be utilized to capture sound from a direction that corresponds to an object zoomed upon by the camera system.

33 Claims, 3 Drawing Sheets

U.S. PATENT DOCUMENTS

| | | |
|---|---|---|
| 5,762,458 A | 6/1998 | Wang et al. |
| 5,786,846 A | 7/1998 | Hiroaki |
| 5,802,494 A | 9/1998 | Kuno |
| 5,917,958 A | 6/1999 | Nunally et al. |
| 5,927,423 A | 7/1999 | Wada et al. |
| 5,959,423 A | 9/1999 | Nakanishi et al. |
| 5,966,130 A | 10/1999 | Benman, Jr. |
| 6,133,944 A | 10/2000 | Braun et al. |
| 6,135,228 A | 10/2000 | Asada et al. |
| 6,211,903 B1 | 4/2001 | Bullister |
| 6,219,587 B1 | 4/2001 | Ahlin et al. |
| 6,232,735 B1 | 5/2001 | Baba et al. |
| 6,233,504 B1 | 5/2001 | Das et al. |
| 6,256,556 B1 | 7/2001 | Zenke |
| 6,259,806 B1 | 7/2001 | Green |
| 6,292,713 B1 | 9/2001 | Jouppi et al. |
| 6,304,050 B1 | 10/2001 | Skaar et al. |
| 6,321,137 B1 | 11/2001 | De Smet |
| 6,325,756 B1 | 12/2001 | Webb et al. |
| 6,330,486 B1 * | 12/2001 | Padula ............................. 700/94 |
| 6,330,493 B1 | 12/2001 | Takahashi et al. |
| 6,346,950 B1 | 2/2002 | Jouppi |
| 6,369,847 B1 | 4/2002 | James et al. |
| 6,430,471 B1 | 8/2002 | Kintou et al. |
| 6,430,475 B2 | 8/2002 | Okamoto et al. |
| 6,438,457 B1 | 8/2002 | Yokoo et al. |
| 6,463,361 B1 | 10/2002 | Wang et al. |
| 6,466,844 B1 | 10/2002 | Ikeda et al. |
| 6,491,701 B2 | 12/2002 | Tierney et al. |
| 6,496,099 B2 | 12/2002 | Wang et al. |
| 6,507,773 B2 | 1/2003 | Parker et al. |
| 6,522,906 B1 | 2/2003 | Salisbury et al. |
| 6,532,404 B2 | 3/2003 | Colens |
| 6,535,182 B2 | 3/2003 | Stanton |
| 6,535,793 B2 | 3/2003 | Allard |
| 6,540,039 B1 | 4/2003 | Yu et al. |
| 6,543,899 B2 | 4/2003 | Covannon et al. |
| 6,549,215 B2 | 4/2003 | Jouppi |
| 6,604,019 B2 | 8/2003 | Ahlin et al. |
| 6,646,677 B2 | 11/2003 | Noro et al. |
| 6,684,129 B2 | 1/2004 | Salisbury et al. |
| 6,691,000 B2 | 2/2004 | Nagai et al. |
| 6,728,599 B2 | 4/2004 | Wright et al. |
| 6,781,606 B2 | 8/2004 | Jouppi |
| 6,784,916 B2 | 8/2004 | Smith |
| 6,799,065 B1 | 9/2004 | Niemeyer |
| 6,799,088 B2 | 9/2004 | Wang et al. |
| 6,804,656 B1 | 10/2004 | Rosenfeld et al. |
| 6,836,703 B2 | 12/2004 | Wang et al. |
| 6,839,612 B2 | 1/2005 | Sanchez et al. |
| 6,840,904 B2 | 1/2005 | Goldberg |
| 6,845,297 B2 | 1/2005 | Allard |
| 6,852,107 B2 | 2/2005 | Wang et al. |
| 6,871,117 B2 | 3/2005 | Wang et al. |
| 6,879,879 B2 | 4/2005 | Jouppi et al. |
| 6,892,112 B2 | 5/2005 | Wang et al. |
| 6,895,305 B2 | 5/2005 | Lathan et al. |
| 6,914,622 B1 | 7/2005 | Smith et al. |
| 6,925,357 B2 | 8/2005 | Wang et al. |
| 6,995,664 B1 | 2/2006 | Darling |
| 7,115,102 B2 | 10/2006 | Abbruscato |
| 7,123,285 B2 | 10/2006 | Smith et al. |
| 7,129,970 B2 | 10/2006 | James et al. |
| 7,151,982 B2 | 12/2006 | Liff et al. |
| 7,154,526 B2 | 12/2006 | Foote et al. |
| 7,155,306 B2 | 12/2006 | Haitin et al. |
| 7,156,809 B2 | 1/2007 | Quy |
| 7,161,322 B2 | 1/2007 | Wang et al. |
| 7,164,969 B2 | 1/2007 | Wang et al. |
| 7,171,286 B2 * | 1/2007 | Wang et al. .................... 700/248 |
| 7,174,238 B1 | 2/2007 | Zweig |
| 7,184,559 B2 | 2/2007 | Jouppi |
| 7,188,000 B2 | 3/2007 | Chiappetta et al. |
| 7,215,786 B2 * | 5/2007 | Nakadai et al. .............. 381/94.1 |
| 7,256,708 B2 | 8/2007 | Rosenfeld |
| 7,262,573 B2 | 8/2007 | Wang et al. |
| 2001/0010053 A1 | 7/2001 | Ben-Shachar et al. |
| 2001/0037163 A1 | 11/2001 | Allard |
| 2001/0054071 A1 | 12/2001 | Loeb |
| 2002/0027597 A1 | 3/2002 | Sachau |
| 2002/0057279 A1 | 5/2002 | Jouppi |
| 2002/0058929 A1 | 5/2002 | Green |
| 2002/0063726 A1 | 5/2002 | Jouppi |
| 2002/0120362 A1 | 8/2002 | Lathan et al. |
| 2002/0130950 A1 | 9/2002 | James et al. |
| 2002/0141595 A1 | 10/2002 | Jouppi |
| 2002/0183894 A1 | 12/2002 | Wang et al. |
| 2003/0048481 A1 | 3/2003 | Kobayashi |
| 2003/0050733 A1 | 3/2003 | Wang et al. |
| 2003/0060808 A1 | 3/2003 | Wilk |
| 2003/0100892 A1 | 5/2003 | Morley et al. |
| 2003/0114962 A1 | 6/2003 | Niemeyer |
| 2003/0135203 A1 | 7/2003 | Wang et al. |
| 2003/0144579 A1 | 7/2003 | Buss |
| 2003/0144649 A1 | 7/2003 | Ghodoussi et al. |
| 2003/0151658 A1 | 8/2003 | Smith |
| 2003/0220541 A1 | 11/2003 | Salisbury et al. |
| 2004/0019406 A1 * | 1/2004 | Wang et al. .................... 700/231 |
| 2004/0088077 A1 | 5/2004 | Jouppi et al. |
| 2004/0117065 A1 | 6/2004 | Wang et al. |
| 2004/0143421 A1 | 7/2004 | Wang et al. |
| 2004/0162637 A1 | 8/2004 | Wang et al. |
| 2004/0167666 A1 | 8/2004 | Wang et al. |
| 2004/0167668 A1 | 8/2004 | Wang et al. |
| 2004/0174129 A1 | 9/2004 | Wang et al. |
| 2004/0215490 A1 | 10/2004 | Duchon et al. |
| 2005/0021182 A1 | 1/2005 | Wang et al. |
| 2005/0021183 A1 | 1/2005 | Wang et al. |
| 2005/0021187 A1 | 1/2005 | Wang et al. |
| 2005/0024485 A1 | 2/2005 | Castles et al. |
| 2005/0027794 A1 | 2/2005 | Decker |
| 2005/0028221 A1 | 2/2005 | Liu et al. |
| 2005/0035862 A1 | 2/2005 | Wildman et al. |
| 2005/0038416 A1 | 2/2005 | Wang et al. |
| 2005/0038564 A1 | 2/2005 | Burick et al. |
| 2005/0052527 A1 | 3/2005 | Remy et al. |
| 2005/0065438 A1 | 3/2005 | Miller |
| 2005/0065659 A1 | 3/2005 | Tanaka et al. |
| 2005/0110867 A1 | 5/2005 | Schulz |
| 2005/0204438 A1 | 9/2005 | Wang et al. |
| 2006/0007943 A1 | 1/2006 | Fellman |
| 2006/0013263 A1 | 1/2006 | Fellman |
| 2006/0029065 A1 | 2/2006 | Fellman |
| 2006/0047365 A1 | 3/2006 | Ghodoussi et al. |
| 2006/0064212 A1 | 3/2006 | Thorne |
| 2006/0082642 A1 | 4/2006 | Wang et al. |
| 2006/0098573 A1 | 5/2006 | Beer et al. |
| 2006/0104279 A1 | 5/2006 | Fellman et al. |
| 2006/0259193 A1 | 11/2006 | Wang et al. |
| 2007/0064092 A1 | 3/2007 | Sandbeg et al. |
| 2007/0120965 A1 | 5/2007 | Sandberg et al. |
| 2007/0192910 A1 | 8/2007 | Vu et al. |
| 2007/0198128 A1 | 8/2007 | Ziegler et al. |
| 2007/0199108 A1 | 8/2007 | Angle et al. |
| 2007/0273751 A1 | 11/2007 | Sachau |
| 2009/0030552 A1 * | 1/2009 | Nakadai et al. ................ 700/258 |
| 2010/0116566 A1 * | 5/2010 | Ohm et al. ...................... 180/8.2 |

FOREIGN PATENT DOCUMENTS

| | | |
|---|---|---|
| EP | 0981905 B1 | 1/2002 |
| JP | 07-257422 A | 10/1995 |
| JP | 08-084328 A | 3/1996 |
| JP | 2000-032319 A | 1/2000 |
| JP | 2002-046088 A | 2/2002 |
| JP | 2002-305743 A | 10/2002 |
| WO | WO 2007/041295 | 4/2007 |

OTHER PUBLICATIONS

Bar-Cohen et al., Virtual reality robotic telesurgery simulations using MEMICA haptic system, Mar. 5, 2001, Internet, pp. 1-7.

Bauer, Jeffrey C., "Service Robots in Health Care: The Evolution of Mechanical Solutions to Human Resource Problems", Jun. 2003.

Bauer, John et al., "Remote telesurgical mentoring: feasibility and efficacy", 2000, IEEE, pp. 1-9.

Breslow, Michael J., MD et al., "Effect of a multiple-site intensive care unit telemedicine program on clinical and economic outcome:

An alternative paradigm for intensivist staffing", Critical Care Med, Jan. 2004, vol. 32, No. 1, pp. 31-38.

Brooks, Rodney, Abstracts from Flesh & Machines, How Robots Will Change Us, "Remote Presence", p. 131-147, Feb. 2002.

Celt et al., "The eICU: It's not just telemedicine", Critical Care Medicine, vol. 29, No. 8 (Supplement), Aug. 2001.

Cleary et al., "State of the art in surgical robotics: Clinical applications and technology challenges", Feb. 24, 2002 Internet, pp. 1-26.

CNN, Floating 'droids' to roam space corridors of the future, Jan. 12, 2000, Internet, pp. 1-4.

CNN.com/Technology, Paging R.Robot: Machine helps doctors with patients, Sep. 30, 2003, Internet, 1-3.

Davies, "Robotics in Minimally Invasive Surgery", 1995, Internet, pp. 5/1-5/2.

DiGiorgio, James, "Is Your Emergency Department of the 'Leading Edge'?", 2005, Internet, pp. 1-4.

Elhajj et al., "Supermedia in Internet-based telerobotic operations", 2001, Internet, pp. 1-14.

Fetterman, Videoconferencing over the Internet, 2001, Internet, pp. 1-8.

Goldberg et al., "Collaborative Teleoperation via the Internet", IEEE International Conference on Robotics and Automation, Apr. 2000, San Francisco, California.

Goldman, Lea, "Machine Dreams", Entrepreneurs, Forbes, May 27, 2002.

Gump, Michael D., "Robot Technology Improves VA Pharmacies", 2001, Internet, pp. 1-3.

Harmo et al., "Moving Eye—Interactive Telepresence Over Internet With a Ball Shaped Mobile Robot", 2000.

Hees, William P., "Communications Design for a Remote Presence Robot", Jan. 14, 2002.

F.A. Candelas Herias et al., "Flexible virtual and remote laboratory for teaching Robotics", FORMATEX 2006, Proc. Advance in Control Education, Madrid, Spain, Jun. 21-23, 2006.

Ishihara, Ken et al., "Intelligent Microrobot DDS (Drug Delivery System) Measured and Controlled by Ultrasonics", Nov. 3-5, 1991, IEEE/RSJ, pp. 1145-1150, vol. 2.

Johanson, Supporting video-mediated communication over the Internet, Chalmers University of Technology, Dept of Computer Engineering, Gothenburg, Sweden, 2003.

Jouppi, et al., :Mutually-Immersive Audio Telepresence, Audio Engineering Society Convention Paper, presented at $113^{th}$ Convention Oct. 2002.

Jouppi, Norman P., "First Steps Towards Mutually-Immersive Mobile Telepresence", CSCW '02, Nov. 16-20, 2002, New Orleans LA.

Kanehiro, Fumio et al., Virtual Humanoid Robot Platform to Develop Controllers of Real Humanoid Robots without Porting, 2001, IEEE, pp. 3217-3276.

Lim, Hun-ok et al., Control to Realize Human-like Walking of a Biped Humanoid Robot, IEEE 2000, pp. 3271-3276.

Linebarger, John M. et al., "Concurrency Control Mechanisms for Closely Coupled Collaboration in Multithreaded Virtual Environments", Presence, Special Issue on Advances in Collaborative VEs (2004).

Loeb, Gerald, "Virtual Visit: Improving Communication for Those Who Need It Most", 2001.

Mack, "Minimally invasive and robotic surgery", 2001, Internet IEEE, pp. 568-572.

Martin, Anya, "Days Ahead", Assisted Living Today, vol. 9, Nov./Dec. 2002, pp. 19-22.

McCardle et al., "The challenge of utilizing new technology in design education", 2000 Internet, pp. 122-127.

"More Online Robots, Robots that Manipulate", Internet, http://ford.ieor.berkeley.edu/ir/robots_a2.html, Feb. 2007.

Nakajima et al., "A Multimedia Teleteaching System sing an Electronic Whiteboard for Two-Way Communication of Motion Videos and Chalkboards", 1993, IEEE, pp. 436-441.

Ogata et al., "Development of Emotional Communication Robot: WAMOEBA-2r—Esperimental evaluation . . . ", 2000 IEEE, pp. 175-180.

Ojha, Anad, "An application of Virtual Reality in Rehabilitation", Jan. 1994, IEEE, pp. 4-6.

Paulos et al., "A World Wide Web Telerobotic Remote Environment Browser", http://vive.cs.berkeley.edu/capek, 1995.

Paulos, Eric John, "Personal Tele-Embodiment", Fall 2001.

Paulos, et al. , "Ubiquitous Tele-embodiment: Applications and Implications", International Journal of Human Computer Studies, Jun. 1997, vol. 46, No. 6, pp. 861-877.

Pin et al., "A New Family of Omnidirectional and Holonomic Wheeled Platforms for Mobile Robots", IEEE, vol. 10, No. 4, Aug. 1994.

Robot Hardware Mobile Robotics Research Group, Edinburgh, "Mobile Robotics Research Group", 2000 Internet, pp. 1-2.

Roy et al., "Towards Personal Service Robots for the Elderly", Internet, Mar. 7, 2002.

Salemi et al, "MILO: Personal robot platform", 2005, Internet, pp. 1-6.

Sandt, Frederic et al., "Perceptions for a Transport Robot in Public Environments", 1997, IROS '97.

Shimoga et al., Touch and force reflection for telepresence surgery, 1994, IEEE, pp. 1049-1050.

Stephenson, Gary, "Dr. Robot Tested at Hopkins", Aug. 5, 2003, Internet, pp. 1-2.

Stoianovici et al., "Robotic Tools for Minimally Invasive Urologic Surgery", Dec. 2002, Internet, 1-17.

Tendick et al., "Human-Machine Interfaces for Minimally Invasive Surgery", 1997, IEEE, pp. 2771-2776.

Thrun et al, "Probabilistic Algorithms and the Interactive Museum Tour-Guide Robot Minerva", 2000, Internet pp. 1-35.

Tzafestas, et al., "VR-based Teleoperation of a Mobile Robotic Assistant: Progress Report", 2000, Internet, pp. 1-23.

Urquhart, Kim, "InTouch's robotic Companion 'beams up' healthcare experts", Medical Device Daily, vol. 7, No. 39, Feb. 27, 2003, p. 1, 4.

Weiss et al., Telework and video-mediated communication: Importance of real-time, interactive communication for workers with disabilities, 1999, Internet, pp. 1-4.

Yamasaki et al., Applying Personal Robots and Active Interface to Video Conference Systems, 1995, Internet, pp. 243-248.

Yong et al., "Robot task execution with telepresence using virtual reality technology", 1998, Internet, pp. 1-9.

Zipperer, Lorri, "Robotic dispensing system", 1999, Internet, pp. 1-2.

Zorn, Benjamin G., "Ubiquitous Telepresence", http://www.cs.colorado.edu/~zorn/ut/vision/vision.html, Mar. 5, 1996.

* cited by examiner

MOBILE TELE-PRESENCE SYSTEM WITH A MICROPHONE SYSTEM

BACKGROUND OF THE INVENTION

1. Field of the Invention

The subject matter disclosed generally relates to the field of mobile two-way teleconferencing.

2. Background Information

Robots have been used in a variety of applications ranging from remote control of hazardous material to assisting in the performance of surgery. For example, U.S. Pat. No. 5,762,458 issued to Wang et al. discloses a system that allows a surgeon to perform minimally invasive medical procedures through the use of robotically controlled instruments. One of the robotic arms in the Wang system moves an endoscope that has a camera. The camera allows a surgeon to view a surgical area of a patient.

Tele-robots such as hazardous waste handlers and bomb detectors may contain a camera that allows the operator to view the remote site. U.S. Pat. No. 6,914,622 issued to Smith et al. and assigned to Telbotics, Inc. ("Telbotics patent") discloses a teleconferencing platform that has both a camera and a monitor. The platform includes mechanisms to both pivot and raise the camera and the monitor. The Telbotics patent has a microphone and a system that automatically swivels the monitor to the origin of sound so that the user's image as displayed by the robot monitor faces a speaker.

There has been marketed a mobile robot introduced by InTouch Technologies, Inc., the assignee of this application, under the trademarks COMPANION and RP-7. The InTouch robot is controlled by a user at a remote station. The remote station may be a personal computer with a joystick that allows the user to remotely control the movement of the robot. Both the robot and remote station have cameras, monitors, speakers and microphones to allow for two-way video/audio communication. The robot camera provides video images to a screen at the remote station so that the user can view the robot's surroundings and move the robot accordingly. It would be desirable to create a microphone system that more closely simulated sound perceived by human errors so that the user experiences a more realistic auditory presence through the robot.

BRIEF SUMMARY OF THE INVENTION

A remote controlled robot system that includes a robot and a remote control station. The robot includes a monitor and a binaural microphone system. The remote control station includes a speaker system coupled to the binaural microphone system.

BRIEF DESCRIPTION OF THE DRAWINGS

FIG. 1A is an illustration showing the relationship of two microphones relative to a monitor of a robot head;

DETAILED DESCRIPTION

Disclosed is a remote controlled robot system that includes a robot and a remote control station. The robot includes a binaural microphone system that is coupled to a speaker system of the remote control station. The binaural microphone system may include a pair of microphones located at opposite sides of a robot head. The location of the microphones roughly coincides with the location of ears on a human body. Such microphone location provides the remote operator with a realistic auditory presence including directionality and distance, as if the operator were actually present at the robot location. The robot may include two different microphone systems and the ability to switch between systems. For example, the robot may also include a zoom camera system and a directional microphone. The directional microphone may be utilized to capture sound from a direction that corresponds to an object zoomed upon by the camera system.

Figure 1:
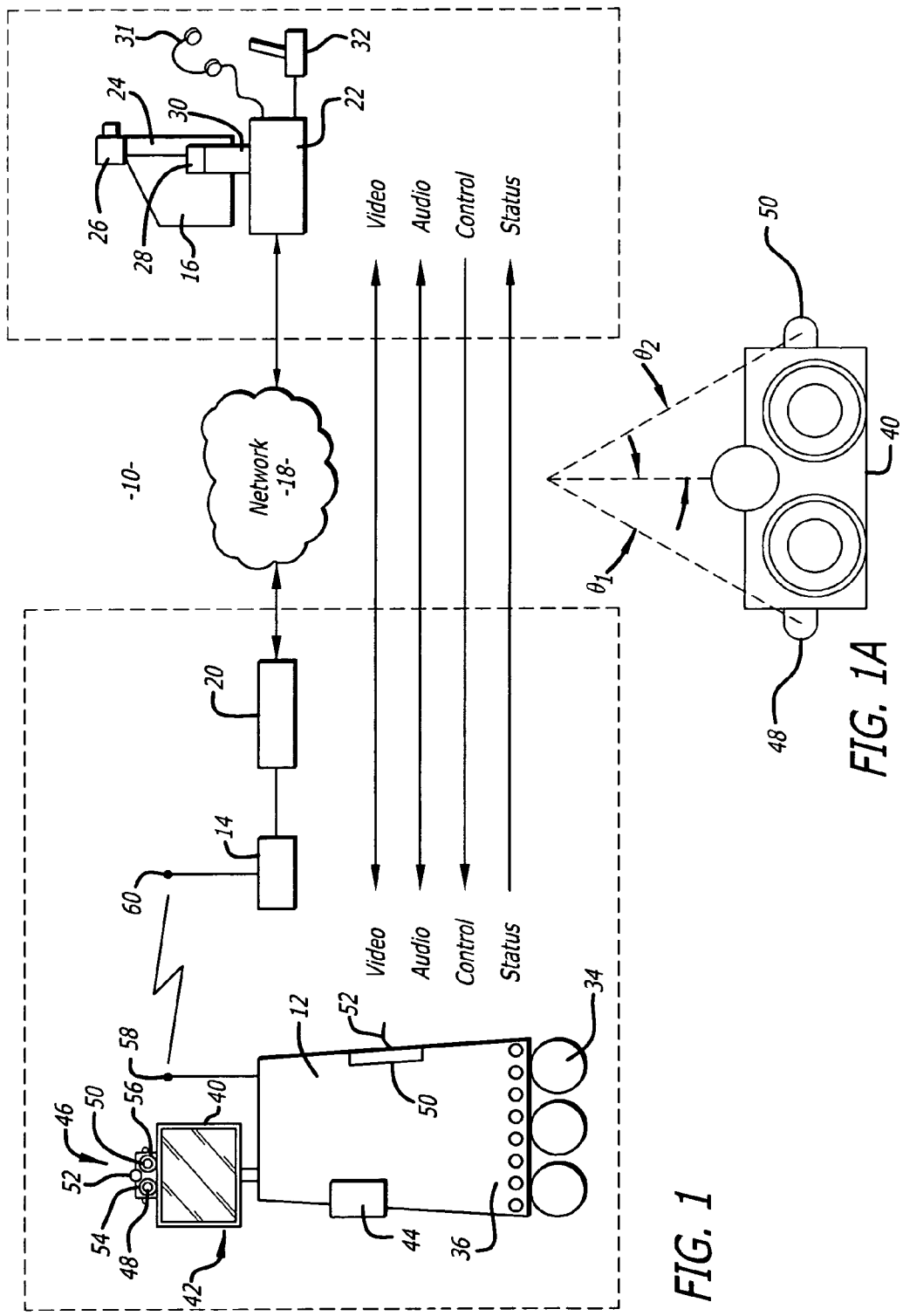
FIG. 1 is an illustration of a robotic system.

Referring to the drawings more particularly by reference numbers, FIG. 1 shows a robotic system 10 that can be used to conduct a remote visit. The robotic system 10 includes a robot 12, a base station 14 and a remote control station 16. The remote control station 16 may be coupled to the base station 14 through a network 18. By way of example, the network 18 may be either a packet switched network such as the Internet, or a circuit switched network such has a Public. Switched Telephone Network (PSTN) or other broadband system. The base station 14 may be coupled to the network 18 by a modem 20 or other broadband network interface device. By way of example, the base station 14 may be a wireless router. Alternatively, the robot 12 may have a direct connection to the network thru for example a satellite.

The remote control station 16 may include a computer 22 that has a monitor 24, a camera 26, a microphone 28 and a speaker 30. The station 16 may also include a headset 31 that can be worn by the user. The computer 22 may have an input device 32 such as a joystick and/or a mouse and a keyboard 33. The control station 16 is typically located in a place that is remote from the robot 12. Although only one remote control station 16 is shown, the system 10 may include a plurality of remote stations. In general any number of robots 12 may be controlled by any number of remote stations 16 or other robots 12. For example, one remote station 16 may be coupled to a plurality of robots 12, or one robot 12 may be coupled to a plurality of remote stations 16, or a plurality of robots 12.

Figure 2:
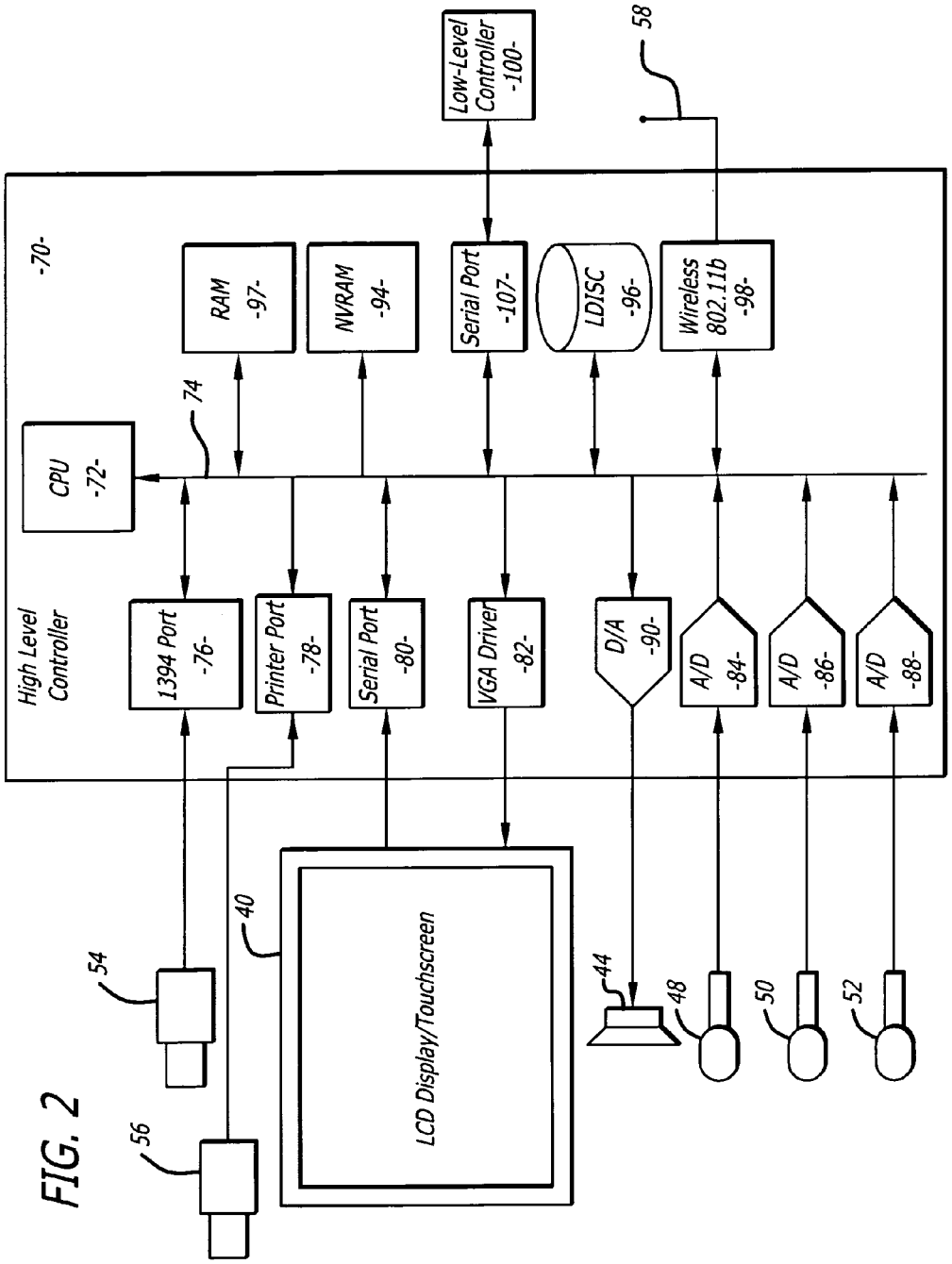
FIG. 2 is a schematic of an electrical system of a robot.

Each robot 12 includes a movement platform 34 that is attached to a robot housing 36. As shown in FIG. 2 each robot 12 may include a monitor 40 that display an image of the operator at the remote control station. The monitor 40 may be part of a robot head 42 that moves relative to the movement platform 34. The head 42 may have a speaker system 44 that generates sound provided by the remote control station.

The robot 12 includes a binaural microphone system 46. The binaural microphone system 46 includes a first microphone 48 located on one side of the head and a second microphone 50 located on another side of the head. The microphones 48 and 50 are located at positions approximately similar to the location of ears on a human body. By way of example, the microphones 48 and 50 can be located about 18 centimeters apart. Utilizing a binaural microphone system 46 creates a robot head that approximates a human head. By way of example, the binaural microphone system 46 may be a matched pair of omni-directional electric condenser microphones. One definition of binaural is that the microphones 48 and 50 are located at positions at approximately equal angles relative to a plane that intersects and is essentially perpendicular to the camera system which is incident with the monitor 40 as shown in FIG. 1A (e.g. $\theta_1 = \theta_2$).

A matched pair of microphones produce an equal voltage for a given sound pressure. The output signals of the microphones may be processed to produce stereo audio channels. An example of a matched microphone system is a product sold by Sound Professionals under the product designation SP-BMC-12. The speaker system of the remote control station may include headphones as shown in FIG. 1.

The robot 12 may also have a directional microphone 52. The directional microphone 52 can be used to capture sound received in a certain direction(s). For example, the directional microphone 52 may be a barrel-like structure that captures sound traveling along a desired axis but impedes off-axis sound. An example, of such a directional microphone is a product sold by Sennheiser under the product designation ME66/K6.

The robot 12 has a camera system. The camera system may include a first camera 54 and a second camera 56. The second camera 56 may include a zoom len(s) and is utilized when the system is in a zoom mode. The first camera 54 may provide images in a non-zoom mode. The system can be configured so that the sound captured by the directional microphone is the sole or primary sound recreated at the remote control station. Although two cameras are shown and described, it is to be understood that the robot may contain only one camera that has the capability to provide a zoom image and a non-zoom image.

The robot 12 may also have an antenna 58 that is wirelessly coupled to an antenna 60 of the base station 14. The system 10 allows a user at the remote control station 16 to move the robot 12 through operation of the input device 32. The robot cameras 54 and 56 are coupled to the remote monitor 24 so that a user at the remote station 16 can view a patient. Likewise, the robot monitor 40 is coupled to the remote camera 26 so that the patient can view the user. The microphones 28 and 48, 50 and 52, and speakers 30 and 44, allow for audible communication between the patient and the user.

The remote station computer 22 may operate Microsoft OS software and WINDOWS XP or other operating systems such as LINUX. The remote computer 22 may also operate a video driver, a camera driver, an audio driver and a joystick driver. The video images may be transmitted and received with compression software such as MPEG CODEC.

FIG. 2 shows an embodiment of a robot 12. Each robot 12 may include a high level control system 70. The high level control system 50 may include a processor 72 that is connected to a bus 74. The bus 74 is coupled to the cameras 54 and 56 by an input/output (I/O) ports 76 and 78, respectively. The monitor 40 is coupled to the bus 74 by a serial output port 80 and a VGA driver 82. The monitor 40 may include a touchscreen function that allows the patient to enter input by touching the monitor screen.

The microphones 48, 50 and 52 are coupled to the bus 74 by digital to analog converters 84, 86 and 88, respectively. The speaker 44 is coupled to the bus 74 by an analog to digital converter 90. The high level controller 70 may also contain random access memory (RAM) device 92, a non-volatile RAM device 94 and a mass storage device 96 that are all coupled to the bus 74. The mass storage device 96 may contain medical files of the patient that can be accessed by the user at the remote control station 16. For example, the mass storage device 96 may contain a picture of the patient. The user, particularly a health care provider, can recall the old picture and make a side by side comparison on the monitor 24 with a present video image of the patient provided by the camera 38. The robot antennae 58 may be coupled to a wireless transceiver 98. By way of example, the transceiver 98 may transmit and receive information in accordance with IEEE 802.11b.

The controller 70 may operate with a LINUX OS operating system. The controller 70 may also operate MS WINDOWS along with video, camera and audio drivers for communication with the remote control station 16. Video information may be transceived using MPEG CODEC compression techniques. The software may allow the user to send e-mail to the patient and vice versa, or allow the patient to access the Internet. In general the high level controller 50 operates to control communication between the robot 12 and the remote control station 16.

The remote control station 16 may include a computer that is similar to the high level controller 50. The computer would have a processor, memory, I/O, software, firmware, etc. for generating, transmitting, receiving and processing information.

The high level controller 70 may be linked to a low level controller 100 by a serial port 102. The low level controller 100 runs software routines that mechanically actuate the robot 12. For example, the low level controller 100 provides instructions to actuate the movement platform to move the robot 12. The low level controller 52 may receive movement instructions from the high level controller 70. The movement instructions may be received as movement commands from the remote control station or another robot. Although two controllers are shown, it is to be understood that each robot 12 may have one controller, or more than two controllers, controlling the high and low level functions.

The robot 12 may have mechanisms so that the monitor 40, cameras 56 and 58 and microphones 48, 50 and 52 all move together in at least two degrees of freedom. Moving the microphones with the cameras insures that the microphone system provides stereophonic sound for all robot head positions. The system may be the same or similar to a robotic system provided by the assignee InTouch-Health, Inc. of Santa Barbara, Calif. under the name RP-6. The system may also be the same or similar to the system disclosed in U.S. Pat. No. 7,158,859 that issued on Jan. 2, 2007, which is hereby incorporated by reference.

Figure 3:
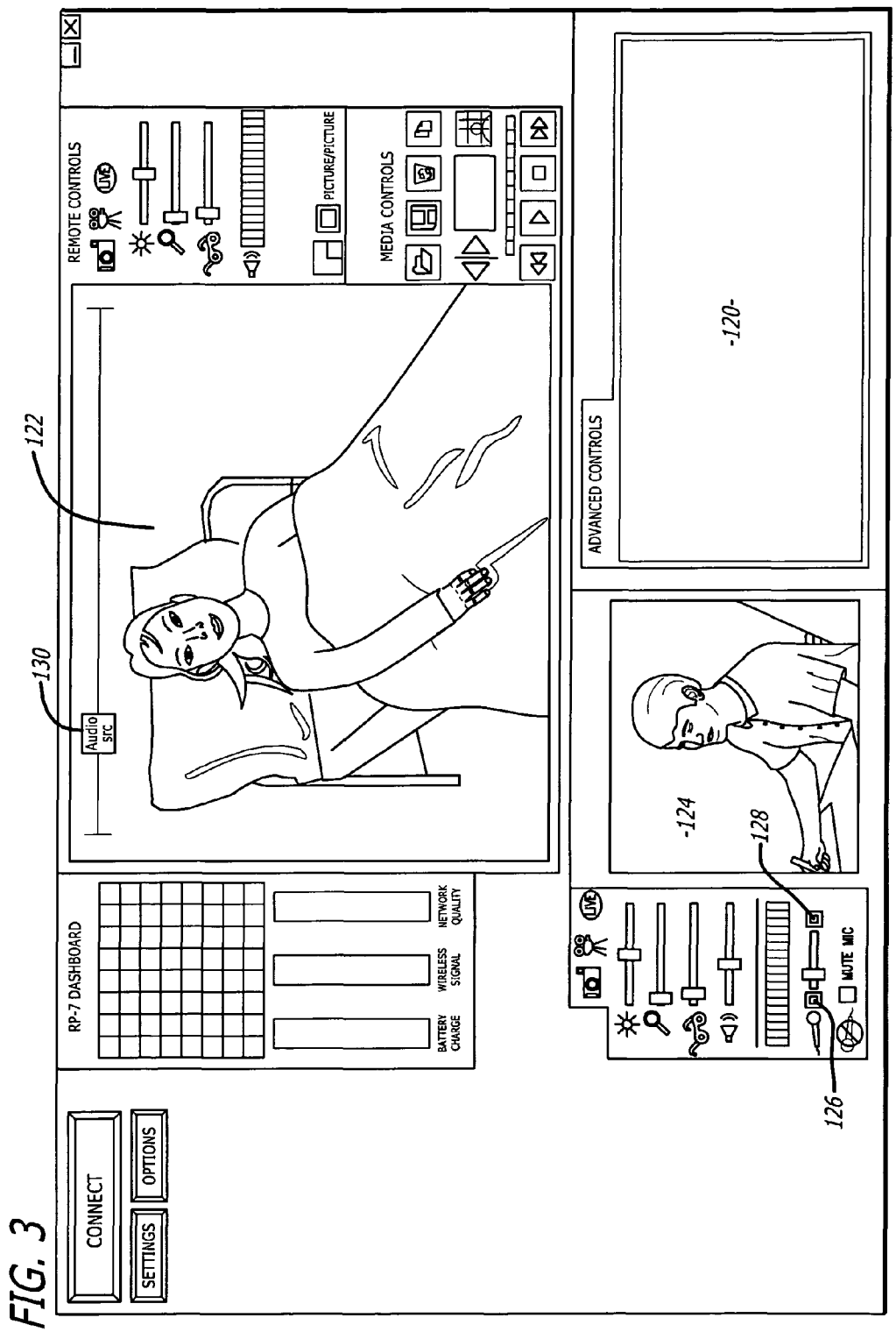
FIG. 3 is a graphical user interface of a remote station.

FIG. 3 shows a display user interface ("DUI") 120 that can be displayed at the remote station 16. The DUI 120 may include a robot view field 122 that displays a video image provided by the camera of the robot. The DUI 120 may also include a station view field 124 that displays a video image provided by the camera of the remote station 16. The DUI 120 may be part of an application program stored and operated by the computer 22 of the remote station 16.

The DUI 120 can include graphical icons 126 and 128 that allow the user to switch between the directional microphone and binaural microphone system, respectively. The DUI 120 may include a graphical overlay 130 in the robot view field 122 that indicates an origin of sound. The position of the overlay 130 corresponds to the sound origin. For example, the position of the overlay 130 shown in FIG. 3 indicates that the origin of sound is to the left of the robot. The user can then move the robot accordingly to improve the volume heard by the microphone system.

The origin of sound can be determined by initially looking at the time of difference between the arrival of sound to both microphones 48 and 50. The peak time $t_d$ can be found in the correlation function $C_{1,2}(t)=X_1(i)*X_2(i+t)$ for all i. An estimate for the angle of arrival (a) can be computed from the trig function $a=\arcsin(v*t_d/d_{1,2})$ where $d_{1,2}$ is the distance between microphones and v is the velocity of sound.

The system may have an automatic mode such that sound captured by the binaural microphone system is reproduced by the remote station when the camera system is in a non-zoom mode and sound captured by the directional microphone is reproduced by the station when the camera system is in a zoom mode. The user can switch between automatic and manual modes by selecting an icon (not shown). A letter "A"

may appear adjacent to the icon when the system is in automatic mode. A letter "M" may appear when the system is in the manual mode.

In operation, the robot 12 may be placed in a home or a facility where one or more patients are to be monitored and/or assisted. The facility may be a hospital or a residential care facility. By way of example, the robot 12 may be placed in a home where a health care provider may monitor and/or assist the patient. Likewise, a friend or family member may communicate with the patient. The cameras and monitors at both the robot and remote control stations allow for teleconferencing between the patient and the person at the remote station(s).

The robot 12 can be maneuvered through the home or a facility by manipulating the input device 32 at a remote station 16. The robot 10 may be controlled by a number of different users. To accommodate for this the robot may have an arbitration system. The arbitration system may be integrated into the operating system of the robot 12. For example, the arbitration technique may be embedded into the operating system of the high-level controller 50.

By way of example, the users may be divided into classes that include the robot itself, a local user, a caregiver, a doctor, a family member, or a service provider. The robot 12 may override input commands that conflict with robot operation. For example, if the robot runs into a wall, the system may ignore all additional commands to continue in the direction of the wall. A local user is a person who is physically present with the robot. The robot could have an input device that allows local operation. For example, the robot may incorporate a voice recognition system that receives and interprets audible commands.

A caregiver is someone who remotely monitors the patient. A doctor is a medical professional who can remotely control the robot and also access medical files contained in the robot memory. The family and service users remotely access the robot. The service user may service the system such as by upgrading software, or setting operational parameters.

The robot 12 may operate in one of two different modes; an exclusive mode, or a sharing mode. In the exclusive mode only one user has access control of the robot. The exclusive mode may have a priority assigned to each type of user. By way of example, the priority may be in order of local, doctor, caregiver, family and then service user. In the sharing mode two or more users may share access with the robot. For example, a caregiver may have access to the robot, the caregiver may then enter the sharing mode to allow a doctor to also access the robot. Both the caregiver and the doctor can conduct a simultaneous tele-conference with the patient.

The arbitration scheme may have one of four mechanisms; notification, timeouts, queue and call back. The notification mechanism may inform either a present user or a requesting user that another user has, or wants, access to the robot. The timeout mechanism gives certain types of users a prescribed amount of time to finish access to the robot. The queue mechanism is an orderly waiting list for access to the robot. The call back mechanism informs a user that the robot can be accessed. By way of example, a family user may receive an e-mail message that the robot is free for usage. Tables I and II, show how the mechanisms resolve access request from the various users.

TABLE I

| User | Access Control | Medical Record | Command Override | Software/Debug Access | Set Priority |
|---|---|---|---|---|---|
| Robot | No | No | Yes (1) | No | No |
| Local | No | No | Yes (2) | No | No |
| Caregiver | Yes | Yes | Yes (3) | No | No |
| Doctor | No | Yes | No | No | No |
| Family | No | No | No | No | No |
| Service | Yes | No | Yes | Yes | Yes |

TABLE II

| | | Requesting User | | | | |
|---|---|---|---|---|---|---|
| | | Local | Caregiver | Doctor | Family | Service |
| Current User | Local | Not Allowed | Warn current user of pending user Notify requesting user that system is in use Set timeout | Warn current user of pending user Notify requesting user that system is in use Set timeout = 5 m | Warn current user of pending user Notify requesting user that system is in use Set timeout = 5 m Call back | Warn current user of pending user Notify requesting user that system is in use No timeout Call back |
| | Caregiver | Warn current user of pending user. Notify requesting user that system is in use. Release control | Not Allowed | Warn current user of pending user Notify requesting user that system is in use Set timeout = 5 m Queue or callback | Warn current user of pending user Notify requesting user that system is in use Set timeout = 5 m | Warn current user of pending user Notify requesting user that system is in use No timeout Callback |
| | Doctor | Warn current user of pending user Notify requesting user that system is in use Release control | Warn current user of pending user Notify requesting user that system is in use Set timeout = 5 m | Warn current user of pending user Notify requesting user that system is in use No timeout Callback | Notify requesting user that system is in use No timeout Queue or callback | Warn current user of pending user Notify requesting user that system is in use No timeout Callback |
| | Family | Warn current user of pending user Notify requesting user that system is in use Release Control | Notify requesting user that system is in use No timeout Put in queue or callback | Warn current user of pending user Notify requesting user that system is in use Set timeout = 1 m | Warn current user of pending user Notify requesting user that system is in use Set timeout = 5 m Queue or callback | Warn current user of pending user Notify requesting user that system is in use No timeout Callback |
| | Service | Warn current user of pending user | Notify requesting user that system is | Warn current user of request | Warn current user of pending user | Not Allowed |

TABLE II-continued

| | Requesting User | | | |
|---|---|---|---|---|
| Local | Caregiver | Doctor | Family | Service |
| Notify requesting user that system is in use<br>No timeout | in use<br>No timeout<br>Callback | Notify requesting user that system is in use<br>No timeout<br>Callback | Notify requesting user that system is in use<br>No timeout<br>Queue or callback | |

The information transmitted between the station 16 and the robot 12 may be encrypted. Additionally, the user may have to enter a password to enter the system 10. A selected robot is then given an electronic key by the station 16. The robot 12 validates the key and returns another key to the station 16. The keys are used to encrypt information transmitted in the session.

The robot 12 and remote station 16 transmit commands through the broadband network 18. The commands can be generated by the user in a variety of ways. For example, commands to move the robot may be generated by moving the joystick 32 (see FIG. 1). The commands are preferably assembled into packets in accordance with TCP/IP protocol. Table III provides a list of control commands that are generated at the remote station and transmitted to the robot through the network.

TABLE III

Control Commands

| Command | Example | Description |
|---|---|---|
| drive | drive 10.0 0.0 5.0 | The drive command directs the robot to move at the specified velocity (in cm/sec) in the (x, y) plane, and turn its facing at the specified rate (degrees/sec). |
| goodbye | goodbye | The goodbye command terminates a user session and relinquishes control of the robot |
| gotoHomePosition | gotoHomePosition 1 | The gotoHomePosition command moves the head to a fixed "home" position (pan and tilt), and restores zoom to default value. The index value can be 0, 1, or 2. The exact pan/tilt values for each index are specified in robot configuration files. |
| head | head vel pan 5.0 tilt 10.0 | The head command controls the head motion. It can send commands in two modes, identified by keyword: either positional ("pos") or velocity ("vol"). In velocity mode, the pan and tilt values are desired velocities of the head on the pan and tilt axes, in degree/sec. A single command can include just the pan section, or just the tilt section, or both. |
| keepalive | keepalive | The keepalive command causes no action, but keeps the communication (socket) link open so that a session can continue. In scripts, it can be used to introduce delay time into the action. |
| odometry | odometry 5 | The odometry command enables the flow of odometry messages from the robot. The argument is the number of times odometry is to be reported each second. A value of 0 turns odometry off. |
| reboot | reboot | The reboot command causes the robot computer to reboot immediately. The ongoing session is immediately broken off. |
| restoreHeadPosition | restoreHeadPosition | The restoreHeadPosition functions like the gotoHomePosition command, but it homes the head to a position previously saved with gotoHomePosition. |
| saveHeadPosition | saveHeadPosition | The saveHeadPosition command causes the robot to save the current head position (pan and tilt) in a scratch location in temporary storage so that this position can be restored. Subsequent calls to "restoreHeadPosition" will restore this saved position. Each call to saveHeadPosition overwrites any previously saved position. |

TABLE III-continued

| | Control Commands | |
|---|---|---|
| Command | Example | Description |
| setCameraFocus | setCameraFocus 100.0 | The setCameraFocus command controls focus for the camera on the robot side. The value sent is passed "raw" to the video application running on the robot, which interprets it according to its own specification. |
| setCameraZoom | setCameraZoom 100.0 | The setCameraZoom command controls zoom for the camera on the robot side. The value sent is passed "raw" to the video application running on the robot, which interprets it according to its own specification. |
| shutdown | Shutdown | The shutdown command shuts down the robot and powers down its computer. |
| stop | stop | The stop command directs the robot to stop moving immediately. It is assumed this will be as sudden a stop as the mechanism can safely accommodate. |
| timing | Timing 3245629 500 | The timing message is used to estimate message latency. It holds the UCT value (seconds + milliseconds) of the time the message was sent, as recorded on the sending machine. To do a valid test, you must compare results in each direction (i.e., sending from machine A to machine B, then from machine B to machine A) in order to account for differences in the clocks between the two machines. The robot records data internally to estimate average and maximum latency over the course of a session, which it prints to log files. |
| userTask | userTask "Jane Doe" "Remote Visit" | The userTask command notifies the robot of the current user and task. It typically is sent once at the start of the session, although it can be sent during a session if the user and/or task change. The robot uses this information for record-keeping. |

Table IV provides a list of reporting commands that are generated by the robot and transmitted to the remote station through the network.

TABLE IV

| | Reporting Commands | |
|---|---|---|
| Command | Example | Description |
| abnormalExit | abnormalExit | This message informs the user that the robot software has crashed or otherwise exited abnormally. Te robot software catches top-level exceptions and generates this message if any such exceptions occur. |
| bodyType | bodyType 3 | The bodyType message informs the station which type body (using the numbering of the mechanical team) the current robot has. This allows the robot to be drawn correctly in the station user interface, and allows for any other necessary body-specific adjustments. |
| driveEnabled | driveEnabled true | This message is sent at the start of a session to indicate whether the drive system is operational. |
| emergencyShutdown | emergencyShutdown | This message informs the station that the robot software has detected a possible "runaway" condition (an failure causing the robot to move out of control) and is shutting the entire system down to prevent hazardous motion. |

TABLE IV-continued

Reporting Commands

| Command | Example | Description |
| --- | --- | --- |
| odometry | odometry 10 20 340 | The odometry command reports the current (x, y) position (cm) and body orientation (degrees) of the robot, in the original coordinate space of the robot at the start of the session. |
| sensorGroup | group_data | Sensors on the robot are arranged into groups, each group of a single type (bumps, range sensors, charge meter, etc.) The sensorGroup message is sent once per group at the start of each session. It contains the number, type, locations, and any other relevant data for the sensors in that group. The station assumes nothing about the equipment carried on the robot; everything it knows about the sensors comes from the sensorGroup messages. |
| sensorState | groupName state data | The sensorState command reports the current state values for a specified group of sensor. The syntax and interpretation for the state data is specific to each group. This message is sent once for each group at each sensor evaluation (normally several times per second). |
| systemError | systemError driveController | This message informs the station user of a failure in one of the robot's subsystems. The error_type argument indicates which subsystem failed, including driveController, sensorController, headHome. |
| systemInfo | systemInfo wireless 45 | This message allows regular reporting of information that falls outside the sensor system such as wireless signal strength. |
| text | text "This is some text" | The text string sends a text string from the robot to the station, where the string is displayed to the user. This message is used mainly for debugging. |
| version | version 1.6 | This message identifies the software version currently running on the robot. It is sent once at the start of the session to allow the station to do any necessary backward compatibility adjustments. |

The processor 72 of the robot high level controller 70 may operate a program that determines whether the robot 12 has received a robot control command within a time interval. For example, if the robot 12 does not receive a control command within 2 seconds then the processor 54 provides instructions to the low level controller 50 to stop the robot 12. Although a software embodiment is described, it is to be understood that the control command monitoring feature could be implemented with hardware, or a combination of hardware and software. The hardware may include a timer that is reset each time a control command is received and generates, or terminates, a command or signal, to stop the robot.

The remote station computer 22 may monitor the receipt of video images provided by the robot camera. The computer 22 may generate and transmit a STOP command to the robot if the remote station does not receive or transmit an updated video image within a time interval. The STOP command causes the robot to stop. By way of example, the computer 22 may generate a STOP command if the remote control station does not receive a new video image within 2 seconds. Although a software embodiment is described, it is to be understood that the video image monitoring feature could be implemented with hardware, or a combination of hardware and software. The hardware may include a timer that is reset each time a new video image is received and generates, or terminates, a command or signal, to generate the robot STOP command.

The robot may be a robot head that can both pivot and spin the camera 38 and the monitor 40. Such a head is described in the '859 patent. The robot head 350 may be in the system either with or instead of the mobile robot 12. The robot head can be particularly useful for doctor proctoring. The head can be located at a medical facility such as an emergency room or a doctor's office. A doctor at the remote location can assist in the diagnosis and medical treatment of a patient located at the robot location. The doctor can move the head to view the patient through control commands from the remote control station. Doctor proctoring can also be performed with a mobile robot 12.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:
1. A remote controlled robot system, comprising:
  a robot with a camera system, a directional microphone and a binaural microphone system that captures a sound, said camera system can switch between zoom and non-zoom modes, said directional microphone is utilized when said camera system is in said zoom mode; and, a remote control station that transmits commands to control said robot, said remote control station includes a speaker system that is coupled to said binaural microphone system to generate said sound captured by said binaural microphone and a monitor coupled to said robot camera.

2. The system of claim 1, wherein said camera system and said binaural microphone system are attached to a robot head that can move in at least two degrees of freedom, said binaural microphone system including a first microphone located on a first side of said head and a second microphone located on a second side of said head.

3. The system of claim 1, wherein said binaural microphone system includes a first microphone and a second microphone that are spaced at approximately equal angles relative to a plane that intersects said camera system.

4. The system of claim 1, wherein said remote control station monitor displays a display user interface, said display user interface includes a graphical interface that can be used to switch between said binaural microphone system and said directional microphone.

5. The system of claim 2, wherein said remote control station monitor displays a display user interface, said display user interface provides a graphical depiction of an origin of sound.

6. The system of claim 1, wherein said robot includes a mobile platform.

7. The system of claim 1, wherein said robot includes a monitor that is coupled to a camera of said remote control station.

8. A method for hearing sound produced at a site of a robot, comprising:
    capturing sound with a binaural microphone system of a robot that has a camera system and a directional microphone;
    transmitting the sound captured by the binaural microphone system to a remote control station;
    switching the camera system of the robot between zoom and non-zoom modes;
    capturing sound with the directional microphone when the camera system is in the zoom mode; and,
    transmitting the sound captured by the directional microphone to the remote control station.

9. The method of claim 8, further comprising displaying a display user interface on a monitor of the remote control station, the display user interface includes a graphical interface that can be used to switch between the binaural microphone system and the directional microphone.

10. The method of claim 8, further comprising displaying a display user interface on a monitor of the remote control station, the display user interface provides a graphical depiction of an origin of sound.

11. The method of claim 8, further comprising moving the robot across a surface.

12. A method for hearing sound produced at a site of a robot, comprising:
    capturing sound with a microphone system of a robot that is coupled to a robot head that has a camera system and a directional microphone, said camera system can switch between zoom and non-zoom modes, said directional microphone is utilized when said camera system is in said zoom mode;
    converting the sound into a plurality of audio channels;
    transmitting the sound to a remote control station;
    producing the sound at the remote control station; moving the robot head;
    switching the camera system of the robot between zoom and non-zoom modes; and
    producing the sound captured by the directional microphone when the camera system is in the zoom mode.

13. The method of claim 12, further comprising displaying a display user interface on a monitor of the remote control station, the display user interface provides a graphical depiction of an origin of sound.

14. The method of claim 12, further comprising moving the robot across a surface.

15. A remote controlled robot system, comprising:
    a robot with a camera system and a microphone system with a directional microphone and a binaural microphone system that capture a sound, said camera system can switch between zoom and non-zoom modes, said directional microphone is utilized when said camera system is in said zoom mode; and,
    a remote control station that transmits commands to control said robot, said remote control station includes a speaker system that is coupled to said microphone system, said remote control station further includes a monitor that displays a display user interface with a graphical depiction of an origin of sound.

16. The system of claim 15, wherein said camera system and said microphone system are attached to a robot head that can move in at least two degrees of freedom, said microphone system including a first microphone located on a first side of said head and a second microphone located on a second side of said head.

17. The system of claim 16, wherein said first and second microphones are spaced at approximately equal angles relative to a plane that intersects said camera system.

18. The system of claim 15, wherein said display user interface includes a graphical interface that can be used to switch between said binaural microphone system and said directional microphone.

19. The system of claim 15, wherein said robot includes a mobile platform.

20. The system of claim 15, wherein said robot includes a monitor that is coupled to a camera of said remote control station.

21. A remote controlled robot system, comprising:
    a robot with a camera system, a binaural microphone system and a directional microphone; and,
    a remote control station that transmits commands to control said robot, said remote control station having a speaker system and switches a speaker output between said binaural microphone system and said directional microphone.

22. The system of claim 21, wherein said binaural microphone system includes a first microphone and a second microphone that are spaced at approximately equal angles relative to a plane that intersects said camera system.

23. The system of claim 21, wherein said robot camera system can switch between zoom and non-zoom modes, said directional microphone is utilized when said camera system is in said zoom mode.

24. The system of claim 21, wherein said remote control station includes a monitor that displays a display user interface, said display user interface includes a graphical interface that can be used to switch between said binaural microphone system and said directional microphone.

25. The system of claim 21, wherein said robot includes a monitor that is coupled to a camera of said remote control station.

26. A remote controlled robot system, comprising:
a robot with a camera system, a first microphone system and a second microphone system; and,
a remote control station that transmits commands to control said robot, said remote control station having a speaker system and switches a speaker output between said first and second microphone systems, said remote control station includes a monitor that displays a display user interface with a graphical interface that can be used to switch between said first and second microphone systems.

27. The system of claim 26, wherein said first microphone system includes a binaural microphone system and said second microphone system includes a directional microphone.

28. A remote controlled robot system, comprising:
a robot with a camera system, a directional microphone and a binaural microphone system that captures a sound, said camera system can switch between zoom and non-zoom modes, said directional microphone is utilized when said camera system is in said zoom mode;
a remote control station that transmits commands to control said robot, said remote control station includes a speaker system that is coupled to said binaural microphone system to generate said sound captured by said binaural microphone and a monitor coupled to said robot camera, said monitor displays a display user interface, said display user interface includes a graphical interface that can be used to switch between said binaural microphone system and said directional microphone.

29. The system of claim 28, wherein said monitor displays a display user interface, said display user interface provides a graphical depiction of an origin of sound.

30. A method for hearing sound produced at a site of a robot, comprising:
capturing sound with a binaural microphone system of a robot that has a camera system and a directional microphone;
transmitting the sound captured by the binaural microphone system to a remote control station;
switching the camera system of the robot between zoom and non-zoom modes;
capturing sound with the directional microphone when the camera system is in the zoom mode;
transmitting the sound captured by the directional microphone to the remote control station; and,
displaying a display user interface on a monitor of the remote control station, the display user interface includes a graphical interface that can be used to switch between the binaural microphone system and the directional microphone.

31. The method of claim 30, further comprising displaying a display user interface on a monitor of the remote control station, the display user interface provides a graphical depiction of an origin of sound.

32. A remote controlled robot system, comprising:
a robot with a camera system and a microphone system with a directional microphone; and,
a remote control station that transmits commands to control said robot, said remote control station includes a speaker system that is coupled to said microphone system, said remote control station further includes a monitor that displays a display user interface with a graphical depiction of an origin of sound, said display user interface includes a graphical interface that can be used to switch between said binaural microphone system and said directional microphone.

33. A remote controlled robot system, comprising:
a robot with a camera system, a binaural microphone system and a directional microphone; and,
a remote control station that transmits commands to control said robot, said remote control station having a speaker system and switches a speaker output between said binaural microphone system and said directional microphone.

* * * * *